(12) United States Patent
Ham et al.

(10) Patent No.: US 10,933,033 B2
(45) Date of Patent: Mar. 2, 2021

(54) COMPOSITION FOR PREVENTING OR REDUCING NEPHROTOXICITY AND USE THEREOF

(71) Applicant: KOREA INSTITUTE OF SCIENCE AND TECHNOLOGY, Seoul (KR)

(72) Inventors: Jungyeob Ham, Gangneung-si (KR); Young Tae Park, Gangneung-si (KR); Taejung Kim, Gangneung-si (KR); Young seok Kim, Gangneung-si (KR); Pilju Choi, Gangneung-si (KR); Kyusun Kim, Gangneung-si (KR); SeonJun Choi, Gangneung-si (KR); BongGeun Song, Gangneung-si (KR); Kisung Kang, Seongnam-si (KR); Buyng Su Hwang, Sangju-si (KR); Dahae Lee, Jinju-si (KR); Jihoon Song, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 3 days.

(21) Appl. No.: 16/282,203

(22) Filed: Feb. 21, 2019

(65) Prior Publication Data
US 2019/0254989 A1 Aug. 22, 2019

(30) Foreign Application Priority Data
Feb. 22, 2018 (KR) ........................ 10-2018-0021205

(51) Int. Cl.
| | | |
|---|---|---|
| *A61K 31/122* | (2006.01) | |
| *A61K 33/243* | (2019.01) | |
| *A61P 13/12* | (2006.01) | |
| *A61K 36/062* | (2006.01) | |
| *A61K 31/05* | (2006.01) | |
| *A61K 31/09* | (2006.01) | |

(52) U.S. Cl.
CPC ............ *A61K 31/122* (2013.01); *A61K 31/05* (2013.01); *A61K 31/09* (2013.01); *A61K 33/243* (2019.01); *A61K 36/062* (2013.01); *A61P 13/12* (2018.01); *A61K 2236/33* (2013.01)

(58) Field of Classification Search
None
See application file for complete search history.

(56) References Cited

U.S. PATENT DOCUMENTS

2018/0280456 A1* 10/2018 Ham .................... A61K 36/062

OTHER PUBLICATIONS

U.S. Appl. No. 15/935,634, filed Mar. 2018, Ham; Jungyeob.*
Fukai et al., "Antiangiogenic Activity of Hypoxylonol C", Journal of Natural Products, 2014, vol. 77, pp. 1065-1068.
Fukai et al., "Hypoxylonols C-F, Benzo[j]fluoranthenes from Hypoxylon truncatum, Journal of Natural Products", 2012, vol. 75, pp. 22-25.
Yokozawa et al., "Effects of Green Tea Tannin on Cisplatin-induced Nephropathy in LLC-PK$_1$ Cells and Rats", J. Pharm. Pharmacol., 1999, vol. 51, pp. 1325-1331.

* cited by examiner

*Primary Examiner* — Michael Barker
(74) *Attorney, Agent, or Firm* — Birch, Stewart, Kolasch & Birch, LLP (57) ABSTRACT

A composition for preventing or reducing nephrotoxicity, and use thereof are provided, the composition including a *Hypoxylon truncatum* extract or an active component thereof.

17 Claims, 5 Drawing Sheets

COMPOSITION FOR PREVENTING OR REDUCING NEPHROTOXICITY AND USE THEREOF

CROSS-REFERENCE TO RELATED APPLICATION

This application claims the benefit of Korean Patent Application No. 10-2018-0021205, filed on Feb. 22, 2018, in the Korean Intellectual Property Office, the disclosure of which is incorporated herein in its entirety by reference.

BACKGROUND

1. Field

One or more embodiments relate to a composition for preventing or reducing nephrotoxicity and use thereof.

2. Description of the Related Art

The kidneys are excretory organs of vertebrates that filter out waste from blood to be excreted as urine. The kidneys are important organs which maintain body homeostasis through waste excretion, and acid/base and electrolyte metabolism. The kidneys filter about 180 L per day, and are thus known as filters in the body. However, for this reason, the kidneys may be a target of toxins which are highly likely to accumulate therein by being carried thereto in the blood. In addition, due to temporary storage of waste in the kidneys during the urine generation process, the kidneys may be in contact with the waste and likely become a target of toxins.

There are various nephrotoxins that cause nephrotoxicity. Chemical substances known to cause nephrotoxicity are non-steroidal anti-inflammatory analgesic agents such as phenacetin, aspirin, and indomethacin; anticancer agents such as puromycin, daunomycin, cyclophosphamide, penicillamine, adriamycin, and cisplatin; immunosuppressants; aminoglycoside antibiotics such as amikacin, gentamycin, kanamycin, neomycin, sisomycin, streptomycin, and tobramycin; cephalosporin antibiotics; carbapenem antibiotics such as imipenem and melopenem; heavy metals such as cadmium, lead, mercury, and chromium, and inorganic and organic heavy metal compounds; compounds such as chloroform, D-serine, sulfonamide, 2-bromoethylene, and hydrobromide; or fungal toxins such as okaratoxin and citrinin. However, most of these compounds are chemical substances or medicines, and the exact mechanisms by which they cause nephrotoxicity are as yet mostly unknown.

Currently, cis-diammine dichloroplatinum II (cisplatin) is being widely used clinically as an anticancer agent for testicular cancer, ovarian cancer, head and neck cancer, bladder cancer, and non-small-cell lung cancer. However, as it accumulates intensively in the kidneys and damages the kidneys, leading to serious toxic side effects, use of cisplatin has been limited.

A number of synthetic formulations for the prevention or treatment of diseases caused by such nephrotoxicity have also been developed. However, due to potential safety issues such as side effects that result when such synthetic formulations are applied to the human body for a long time, the importance of formulations originating from natural substances is emerging.

*Hypoxylon fuscum* belongs to the phylum Ascomycota, the class Sordariomycetes, the order Xylaria, the family Xylaria, and the genus *Hypoxylon*, and its fruiting body has a semicircular or irregularly distorted semicircular shape with a width of about 4 mm to about 5 mm. The chemical structures of hypoxylonol C and hypoxylonol F isolated from *Hypoxylon fuscum* were first reported in 2012, (Miyuki Fukai et al., *Journal of Natural Products*, Vol. 75, p. 22-25, 2012), and, more recently, physiological activities such as the anti-angiogenic effect of hypoxylonol C were also reported by the same researchers (Miyuki Fukai et al., *Journal of Natural Products*, Vol. 77, p. 1065-1068, 2014).

In this regard, there is a need to find new uses of *Hypoxylon truncatum* extracts and active components thereof.

SUMMARY

One or more embodiments include a composition for preventing or reducing nephrotoxicity in a subject, the composition including any stereoisomers of the group consisting of compounds represented by Formulae I, II, and III, or solvates, hydrates, mixtures, or physiologically acceptable salts thereof:

[Formula I]

[Formula II]

and

[Formula III]

wherein, in Formulae I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or $(C_1$-$C_6)$-alkyl.

One or more embodiments include a composition for preventing or reducing apoptosis of kidney cells in a subject, the composition including any stereoisomers selected from the group of compounds represented by Formulae I, II, and III, or solvates, hydrates, mixtures, or physiologically acceptable salts thereof.

One or more embodiments include a method of preventing or reducing damage of kidney cells in a subject, the method including contacting the kidney cells with any of the above-described compositions.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the disclosure, there is provided a composition for preventing or reducing nephrotoxicity in a subject, the composition including any stereoisomers of the group consisting of compounds represented by Formulae I, II, and III, or solvates, hydrates, mixtures, or pharmaceutically acceptable salts thereof:

[Formula I]

[Formula II]

[Formula III]

In Formulae I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or ($C_1$-$C_6$)-alkyl.

In the composition according to one or more embodiments, $R_1$ and $R_5$ may each independently be H or ($C_1$-$C_6$)-alkyl, and $R_2$, $R_3$, $R_4$, $R_5$, $R_6$, $R_7$, $R_8$, $R_9$, $R_{10}$, $R_{11}$, and $R_{12}$ may be H. For example, the ($C_1$-$C_6$)-alkyl may be ($C_1$-$C_5$)-alkyl, ($C_1$-$C_4$)-alkyl, or ($C_1$-$C_3$)-alkyl.

In the composition according to one or more embodiments, $R_1$ and $R_5$ may each independently be H, methyl, or ethyl.

In the composition according to one or more embodiments, the compounds of Formula I, II, and III may be in a weight ratio of about 1.0:0.20 to 0.60:0.50 to 1.00, for example, in a weight ratio of about 1.0:0.32 to 0.52:0.65 to 0.85, or about 1.0:about 0.42:about 0.75.

In one or more embodiments, the composition may include any stereoisomer of the compound of Formula I, II, or III, a salt thereof, and a solvate thereof. With respect to each chiral center, independently of any other chiral centers, the compound of Formula I, II, or III may be in S stereochemical configuration or substantially S stereochemical configuration, or in R stereochemical configuration or substantially R stereochemical configuration, or in a mixture of an S isomer and an R isomer in any ratio. In one or more embodiments, the composition may include any possible enantiomers and diastereoisomers and mixtures of two or more stereoisomers, for example, mixtures of enantiomers and/or diastereoisomers at any ratio. Accordingly, the compound according to one or more embodiments, which may be present as an enantiomer, may be in an enantiomerically pure form, either as the left-handed enantiomer or the right-handed enantiomer, or may exist as a mixture of the two enantiomers in any ratio, including racemates. In one or more embodiments, the compound which may be present in a mixed form of two or more stereoisomers may be pure or substantially pure individual stereoisomers. The individual stereoisomers may be prepared by a common method, for example, by chromatography or crystallization, by separation of a mixture of stereoisomers, by using a stereochemically homogeneous starting material in synthesis, or by stereoselective synthesis. Optionally, before the separation of stereoisomers, derivatization may be performed. The separation of the mixture of stereoisomers may be performed at the stage when the compound of Formula I, II, or III was formed, or at the reaction stage involving a starting material or an intermediate material during synthesis. In one or more embodiments, the composition may include any tautomers of the compound of Formula I, II, or III, salts thereof, and solvates thereof.

When the compound of Formula I, II, or III includes one or more acidic and/or basic groups, i.e., salt-forming groups, the composition according to one or more embodiments may include a pharmaceutically or toxicologically acceptable salt, i.e., a non-toxic salt, and in particular, a pharmaceutically acceptable salt thereof.

In one or more embodiments, the composition may include any solvates of any stereoisomers of the group consisting of the compounds represented by Formula I, II, and III, or for example, hydrates or adducts with alcohol such as ($C_1$-$C_4$)-alkanol, active metabolites of the compound of Formula I, and pro-drugs and derivatives of the compound of Formula I, II, or III, for example, esters or amides of carboxylic acids, which may be converted into a compound that is pharmaceutically active in vivo, though not pharmaceutically active in vitro.

The composition may further include a carrier or diluent which is pharmaceutically acceptable.

The carrier or diluent may be an excipient, a disintegrant, a binder, a lubricant, or a combination thereof. The excipient may be microcrystalline cellulose, lactose, low-substituted hydroxycellulose, or a combination thereof. The disintegrant may be sodium starch glycolate, calcium monohydrogen phosphate anhydrous, or a combination thereof. The binder may be polyvinylpyrrolidone, low-substituted hydroxypropylcellulose, hydroxypropylcellulose, or a combination thereof. The lubricant may be magnesium stearate, silicon dioxide, talc, or a combination thereof.

The composition may be formulated into an oral or parenteral formulation. The oral formulation may include granules, powders, liquids, tablets, capsules, dry syrups, or combinations thereof. The parenteral formulation may be an injectable formulation.

An administration dosage of the composition may vary depends on various factors such as the degree of progression of obesity, the time of onset of a disease, age, health conditions, complications, or the like of a subject to be administered. In one or more embodiments, the administration dosage of the composition may be about 1 µg/kg/day to about 200 mg/kg/day, or about 50 µg/kg/day to 50 mg/kg/day, based on any stereoisomers selected from the group consisting of the compounds represented by Formulae I, II, and III, or solvates, hydrates, mixtures, or pharmaceutically acceptable salts thereof.

The nephrotoxicity may be caused by nephrotoxic material. The nephrotoxic material may block the mitogen-activated protein kinase (MAPK) signaling pathway. The nephrotoxic material may increase phosphorylation of p38, extracellular signal-regulated kinase (ERK), and c-Jun N-terminal kinase (JNK). The nephrotoxic material may increase the level of expression of cleaved caspase-3. The nephrotoxic material may increase apoptosis of kidney cells. The kidney cells may be proximal tubule cells. The nephrotoxic material may be selected from the group consisting of a platinum-based anticancer agent, gentamicin, an iodinated contrast agent, foscarnet mannitol, amphotericin B, acetoaminophen, and chloroform. The platinum-based anticancer agent may be cis-diaminodichloroplatinum II (cis-platin), carboplatin, oxaliplatin, or nedaplatin.

The composition according to one or more embodiments may reduce apoptosis of kidney cells. The kidney cells may be proximal tubule cells.

The nephrotoxicity may cause renal failure such as acute renal failure. Accordingly, the composition according to one or more embodiments may be used to prevent or treat a disease caused by nephrotoxicity.

The composition according to one or more embodiments may further include a material which may cause nephrotoxicity. Details of this material may be the same as described above in connection with the nephrotoxic material. The material which may cause nephrotoxicity may be included as a therapeutic agent, or an imaging agent, but may exhibit nephrotoxicity as a side effect.

The composition according to one or more embodiments may further include an additional therapeutic agent, in addition to the nephrotoxic material.

The composition according to one or more embodiments may be administered before, at the same time as, or after administration of the nephrotoxic material as a therapeutic agent to the subject.

The composition according to one or more embodiments may include a *Hypoxylon* sp. mushroom extract including any stereoisomers of the group consisting of the compounds represented by Formulae I, II, and III, mixtures thereof, or pharmaceutically acceptable salts thereof.

*Hypoxylon* sp. mushroom may be, for example, *Hypoxylon truncatum*, *Hypoxylon fuscum*, *Hypoxylon fragiforme*, or *Hypoxylon tinctor*.

The extract may be obtained by extraction using a method including contacting the *Hypoxylon* sp. mushroom with water, an organic solvent, or a mixture thereof. The contacting may be performed at about 10° C. to reflux temperature. The temperature may be room temperature, about 15° C. to reflux temperature, about 25° C. to reflux temperature, about 40° C. to reflux temperature, about 50° C. to reflux temperature, or about 25° C. to about 70° C.

The organic solvent may be an aqueous or non-aqueous organic solvent. The organic solvent may be a $(C_1$-$C_6)$-alcohol, $R_{13}$—COO—$R_{14}$ (wherein $R_{13}$ and $R_{14}$ may each independently be a $(C_1$-$C_6)$-alkyl), a $(C_4$-$C_{12})$-alkane, acetone, ethyl methyl ketone, acetonitrile, carbon tetrachloride ($CCl_4$), chloroform ($CHCl_3$), dichloromethane ($CH_2Cl_2$), or a mixture thereof. The $(C_1$-$C_6)$-alcohol may be a $(C_1$-$C_3)$-alcohol. The alcohol may be methanol, ethanol, isopropanol, or butanol. In the $R_{13}$—COO—$R_{14}$, $R_{13}$ and $R_{14}$ may each independently be a $(C_1$-$C_3)$-alkyl, a $(C_1$-$C_2)$-alkyl, or methyl. The $R_{13}$—COO—$R_{14}$ may be ethyl acetate. The $(C_4$-$C_{12})$-alkane may be hexane. The organic solvent may be acetone, ethyl methyl ketone, methanol, ethanol, carbon tetrachloride, chloroform, dichloromethane, or a mixed solvent of methanol and dichloromethane.

The contacting time may differ depending on an amount of the sample and a type of the solvent to be used, and may be, for example, about 6 hours to about 48 hours, or about 12 hours to about 24 hours.

The obtained extract may be distilled under reduced pressure to remove the organic solvent, thereby obtaining, for example, a *Hypoxylon truncatum* extract. A temperature of the distillation under reduced pressure may differ depending on a type of the solvent to be used, and may be, for example, about 10° C. to about 40° C., or about 20° C. to about 30° C.

Further, the *Hypoxylon truncatum* extract may be a fraction extract obtained by fractionation based on differences in polarities of solvents. The solvent used in fractionation may be one or more selected from the group consisting of a $(C_4$-$C_{12})$-alkane solvent (for example, hexane), ethyl acetate, butanol, and distilled water. For example, the solvent may be hexane or ethyl acetate.

In one or more embodiments, *Hypoxylon truncatum* may be contacted with ethanol to obtain an ethanol layer. The ethanol layer may then be subjected to distillation under reduced pressure to obtain an ethanol extract. This ethanol extract may be dissolved in water, and then be contacted with hexane to obtain a hexane layer. This hexane layer may be subjected to distillation under reduced pressure to obtain a hexane fraction. A water layer remaining after the distillation to obtain the hexane fraction may be contacted with ethyl acetate to obtain an ethyl acetate layer. The ethyl acetate layer may then be subjected to distillation under reduced pressure to obtain an ethyl acetate fraction. A water layer remaining after the distillation to obtain the ethyl acetate fraction may be contacted with butanol to obtain a butanol layer. The butanol layer may then be subjected to distillation under reduced pressure to obtain a butanol fraction. Finally, the remaining water layer may be subjected to distillation under reduced pressure to obtain a water fraction. As a result, the methanol extract, the hexane fraction, the ethyl acetate fraction, the butanol fraction, and the water fraction may be obtained.

The extract fractions may be isolated and purified by chromatography. The chromatography may be, for example, reverse phase preparative high-performance liquid chromatography (Prep-HPLC).

Isolation conditions of the reverse phase Prep-HPLC may differ depending on the amount of the sample and a size of the column to be used. The reverse phase Prep HPLC may be performed by installing a reverse phase preparative column (Phenomenex Luna C18(2) column having a particle size of 10 μm and a column size of 250 mm×21.20 mm) in a liquid chromatography system (available from Gilson Companion), injecting a solution of the sample dissolved in an initial eluent, and the flowing an eluent as a mixture of methanol and water in a ratio of 50:50 to 100:0 for 60 minutes to 90 minutes.

According to another aspect of the disclosure, there is provided a composition for preventing or reducing apoptosis of kidney cells in a subject, the composition including any stereoisomers selected from the group consisting of compounds represented by Formulae I, II, and III, a solvate thereof, a hydrate thereof, or a mixture thereof, or a pharmaceutically acceptable salt thereof:

[Formula I]

[Formula II]

[Formula III]

In Formulae I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or $(C_1-C_6)$-alkyl.

According to another aspect of the disclosure, there is provided a method of preventing or reducing kidney cell damage in a subject or ex vivo, the method including contacting the composition according to any of the above-described embodiments with kidney cells.

The method may be performed in vitro, ex vivo, or in vivo.

The contacting may include administering the composition to the subject.

The contacting may be incubating the composition together with kidney cells in a medium. The medium may be a liquid or a solid. The medium may a medium capable of growing or maintaining the kidney cells. The kidney cells may be proximal tubule cells.

The method may further include administering a nephrotoxic material to the subject or the medium. Details of the nephrotoxic material may be the same as described above. The nephrotoxic material may be selected from the group consisting of a platinum-based anticancer agent, gentamicin, an iodinated contrast agent, foscarnet, mannitol, amphotericin B, acetoaminophen, and chloroform.

The administering of the composition may be performed before, during, or after the administering of the nephrotoxic material. The kidney cell damage may be apoptosis of kidney cells.

The administration dosage of the composition may be an effective amount for prevention or reduction of kidney cell damage. The effective amount may be about 1 μg/kg/day to about 200 mg/kg/day, or about 50 μg/kg/day to about 50 mg/kg/day, based on any stereoisomers selected from the group consisting of the compounds represented by Formulae I, II, and III, or solvates, hydrates, mixtures, or pharmaceutically acceptable salts thereof.

The administration route may be an oral or parenteral route. The administration may be intramuscular, intraperitoneal, or intravenous administration.

The subject may be a mammal. The mammal may be a human, a cow, a horse, a pig, a cat, a goat, or a dog.

One or more embodiments of the disclosure will now be described in detail with reference to the following examples. However, these examples are only for illustrative purposes and are not intended to limit the scope of the one or more embodiments of the disclosure.

EXAMPLE 1

Preparation of *Hypoxylon truncatum* Extract and Fractions Thereof

*Hypoxylon truncatum* used in this example was a wild type collected in the area of Sogeum River, Yeongok-myeon, Gangneung-si, Gangwon-do, Republic of Korea, and extracted with organic solvents.

Figure 1:
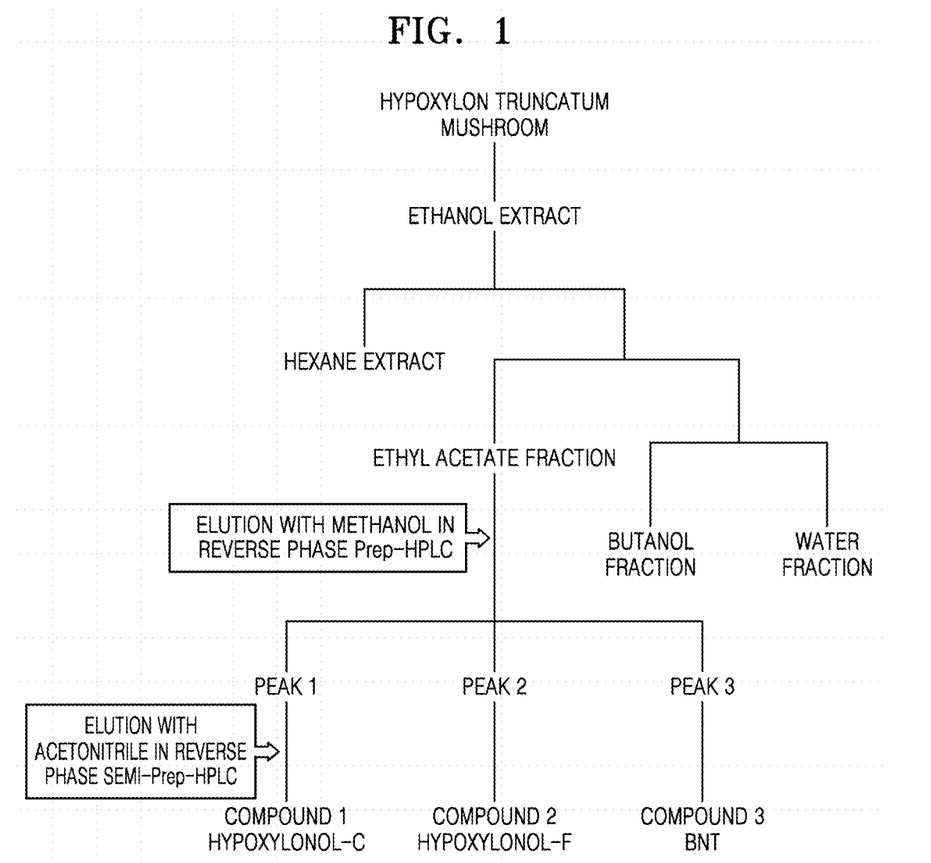
FIG. 1 is a schematic illustration of preparation processes of a *Hypoxylon truncatum* extract and fractions thereof.

FIG. 1 is a schematic illustration of a preparation process of a *Hypoxylon truncatum* extract and fractions thereof. A detailed extraction process is as follows.

1. Preparation of Ethanol Extract

The whole body of *Hypoxylon truncatum* was grinded in a mixer (Model no. NFM-8860, available from NUC, Republic of Korea), and 50 g of the grinded product was put in 500 mL of 100%-ethanol and left at room temperature for 24 hours. This process was repeated twice. The solution was filtered through a filter paper, and the resulting filtrate was distilled under reduced pressure to thereby obtain 6.3 g of a crude extract (hereinafter, referred to as 'ethanol extract.')

Figure 2:
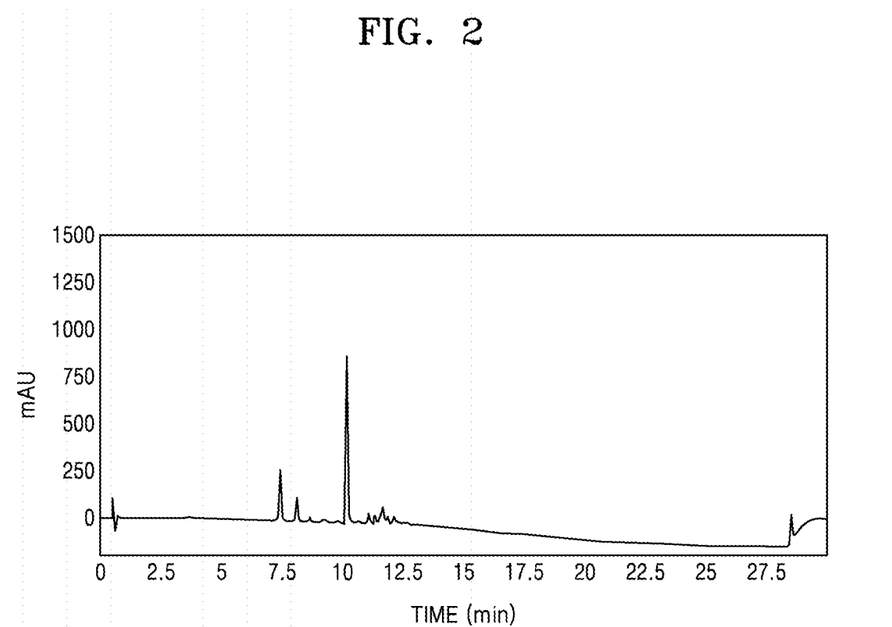
FIG. 2 is a chromatogram showing results of high-performance liquid chromatography (HPLC) analysis of an ethanol extract of *Hypoxylon truncatum*.

FIG. 2 is a chromatogram as a result of HPLC analysis of the ethanol extract of *Hypoxylon truncatum*. The HPLC analysis was performed using Nexera X2 (available from Shimadzu, Japan) and a EVO C18 column (available from Phenomenex) with a particle size of 1.7 μm and a column size of 100 mm×2.1 mm under conditions in which an eluent of acetonitrile at a gradient of 10% at an initial stage to 100% in water was flowed at a flow rate of 0.3 mL/min for 25 minutes.

2. Separation of Hypoxylonol C, Hypoxylonol F, and BNT

Three compounds, including hypoxylonol-C, were separated from the *Hypoxylon truncatum* crude extract prepared as above.

In particular, 5 g of the crude extract was dissolved in 250 mL of water and then mixed with 250 mL of hexane. The resulting mixture was left at room temperature for about 24 hours to separate a supernatant, which was then distilled under reduced pressure. These processes were repeated three times to thereby separate a hexane fraction. The remaining water layer was mixed with 250 mL of ethyl acetate and then left at room temperature for about 24 hours to separate a supernatant, which was then distilled under reduced pressure. These processes were repeated three times to thereby separate an ethyl acetate fraction. The remaining water layer was mixed with 250 mL of butanol and then left at room temperature for about 24 hours to separate a supernatant, which was then distilled under reduced pressure. These processes were repeated three times to thereby separate a butanol fraction and a water fraction.

The ethyl acetate fraction was eluted from a reverse phase Prep-HPLC system (available from Phenomenex, Luna C18 (2) column with a particle size of 10 μm and a column size of 250 mm×21.20 mm) while methanol as an eluent at a gradient of 50% at an initial stage to 100% in water was flowed at a flow rate of about 8 mL/min for about 60 minutes to about 90 minutes. As a result, a chromatogram as represented in FIG. 2 was obtained in which three peaks were detected at a UV wavelength of 230 nm. Fractions corresponding to the three peaks were eluted from the column in a reverse phase semi-Prep-HPLC (available from Phenomenex, a Gemini 6 Phenyl column having a particle size of 5 μm and a column size of 250 mm×10 mm) while an acetonitrile gradient from 50% at initial state to 100% in water was flowed as an eluent at a flow rate of about 4 mL/min for about 60 minutes to about 90 minutes. As a result, the three peaks in the chromatogram was identified to be 158 mg of hypoxylonol C, 67 mg of hypoxylonol F, and 119 mg of BNT (1,1'-binaphthalene-4,4',5,5'-tetrol).

Structures of the compounds were identified using nuclear magnetic resonance spectrometry (NMR) and mass spectroscopy. $^{1}$H-NMR and $^{13}$C-NMR spectra of the compounds were obtained using a Bruker AVACE III 400-MHz spectrometer (available from Bruker, Germany) to identify their structure. Chemical formulae and $^{1}$H-NMR and $^{13}$C-NMR data of the isolated compounds are as follows.

[Formula IV]

[Formula V]

[Formula VI]

Formula IV Compound: Hypoxylonol C
$^{1}$H-NMR (400 MHz, Acetone-$d_6$) δ12.6 (s, 1H, OH-9), 8.61 (s, 1H, OH-4), 7.54 (t, 1H, H-11), 7.48 (dd, 1H, H-12), 7.28 (d, 1H, H-6), 6.84 (dd, 1H, H-10), 6.68 (d, 1H, H-5), 5.59 (dd, 1H, H-1), 5.48 (m, 1H, H-3), 5.14 (brd, 1H, OH-3), 4.28 (s, 1H, OH-1), 4.11 (dd, 1H, H-6b), 3.38 (dd, 1H, H-7), 2.47 (dt, 1H, H-2), 2.31 (dd, 1H, H-7), 2.14 (ddd, 1H, H-2)
$^{13}$C-NMR (100 MHz, Acetone-$d_6$) δ 205.9 (C-8), 163.5 (C-9), 155.7 (C-4), 144.1 (C-12d), 139.5 (C-12a), 138.1 (C-12c), 137.6 (C-12b), 137.4 (C-11), 136.4 (C-6a), 123.5 (C-6), 120.6 (C-3a), 118.9 (C-12), 117.0 (C-10), 115.6 (C-8a), 114.4 (C-5), 65.4 (C-3), 65.7 (C-1), 59.7 (C-6b), 43.6 (C-7), 42.3 (C-2)

ESI-MS m/z 335.0 [M-H]$^-$.
Formula V Compound: Hypoxylonol F
$^{1}$H-NMR (400 MHz, Acetone-$d_6$) δ12.6 (s, 1H, OH-9), 7.52 (t, 1H, H-11), 7.48 (dd, 1H, H-12), 7.29 (d, 1H, H-6), 6.82 (dd, 1H, H-10), 6.69 (d, 1H, H-5), 5.38 (d, 1H, H-1), 5.36 (d, 1H, H-3), 4.09 (dddd, 1H, H-6b), 3.39 (dd, 1H, H-7), 2.47 (dt, 1H, H-2), 2.34 (dd, 1H, H-7), 2.24 (dt, 1H, H-2)
$^{13}$C-NMR (100 MHz, Acetone-$d_6$) δ 206.3 (C-8), 163.6 (C-9), 155.7 (C-4), 144.3 (C-12d), 139.5 (C-12a), 139.1 (C-12c), 137.5 (C-12b), 137.2 (C-11), 136.7 (C-6a), 123.8 (C-6), 121.0 (C-3a), 120.9 (C-12), 117.0 (C-10), 115.8 (C-8a), 114.7 (C-5), 67.0 (C-3), 65.2 (C-1), 50.2 (C-6b), 43.8 (C-7), 43.3 (C-2)
ESI-MS m/z 335.0 [M-H]$^-$.
Formula VI Compound: BNT, 1,1'-binaphthalene-4,4',5,5'-tetrol
$^{1}$H-NMR (400 MHz, acetone-$d_6$) δ11.04 (brd, 4H, OH-4,5), 7.16 (d, 2H, H-7), 7.07 (t, 2H, H-2), 6.83 (d, 2H, H-3), 6.72 (dd, 2H, H-6), 6.59 (d, 2H, H-8)
$^{13}$C-NMR (100 MHz, acetone-$d_6$) δ 154.4 (C-5), 153.7 (C-4), 135.7 (C-8a), 129.3 (C-1), 128.8 (C-7), 126.9 (C-2), 117.4 (C-8), 114.5 (C-4a), 108.5 (C-6), 108.1 (C-3) ESI-MS m/z 317.1 [M-H]$^-$.

EXAMPLE 2

Determination of Physiological Activities of *Hypoxylon truncatum* Extract and Active Compounds Thereof 1. Evaluation of Protective Effect of *Hypoxylon truncatum* Extract and Active Components Thereof Against Nephrotoxicity (1) Protective Effect of Cisplatin against Nephrotoxicity A protective effect of cisplatin against nephrotoxicity was evaluated with LLC-PK1 (ATCC CL-101™) kidney cells, using a method disclosed in an article (Yokozawa et al., *J. Pharm. Pharmacol.*, 51, p. 1325-1331, 1999).

First, LLC-PK1 cells were cultured in a Dulbecco's modified Eagle's medium (DMEM) (available from Cellgro, Manassas, Va., USA) in which 10% of fetal bovine serum (FBS), 100 units/mL of penicillin G, and 100 μg/mL of streptomycin were added, in an incubator (95% air and 5% $CO_2$) maintained at about 37° C. The used FBS, penicillin G, and streptomycin were purchased from Gibco BRL Life Technologies Inc. The cultured LLC-PK1 cells were dispensed in a 96-well plate at a density of 1×10$^4$ cells in 100 μL of the same DMEM medium per each well and then stabilized for about 22 hours.

Next, after the stabilized sample was added to 90 μL of the same DMEM medium at a predetermined concentration and incubated further for about 2 hours, 10 μL of a medium in which 250 μM cisplatin was previously dissolved was added thereto and incubated for about 24 hours, and 10 μL of a CCK-8 reagent (available from Dojindo Laboratories, Japan) was added to each well and then incubated at about 37° C. After 1 hour, absorbance at a detection wavelength of 450 nm was measured using a BIO-TEK microplate reader (available from Winooski, Vt., USA) to thereby measure cell viability.

Table 1 represents effects of *Hypoxylon truncatum* extract, hypoxylonol C, hypoxylonol F, and BNT in cisplatin-treated kidney endothelial cells (LLC-PK1 cells). When treated with cisplatin at a final concentration of 25 μM, the number of LLC-PK1 cells was reduced to about 50% or less of that in a non-cisplatin treatment group. The *Hypoxylon trunca-*

*tum* extract and the individual active components thereof were found to suppress cell damage caused by the treatment of cisplatin. The *Hypoxylon truncatum* extract, hypoxylonol C, hypoxylonol F, and BNT were found to significantly increase cell viability that had been reduced with the treatment of cisplatin at a final concentration of 25 μM, in a concentration-dependent manner. In particular, hypoxylonol F increased the cell viability to about 90% or greater at a concentration of 10 μM, and hypoxylonol C increased the cell viability to about 85% or greater at the same concentration.

TABLE 1

| Compound | Concentration (μg/mL) | Cell viability (%) |
| --- | --- | --- |
| *Hypoxylon truncatum* extract (Ethanol extract) | 0 | 59.0 |
| | 5 | 60.3 |
| | 10 | 63.8 |
| | 25 | 64.3 |
| | 50 | 73.1 |
| | 100 | 74.8 |
| Hypoxylonol C | 0 | 60.9 |
| | 5 | 76.9 |
| | 10 | 86.6 |
| | 25 | 89.3 |
| | 50 | 89.5 |
| | 100 | 92.5 |
| Hypoxylonol F | 0 | 60.9 |
| | 5 | 86.4 |
| | 10 | 90.9 |
| | 25 | 92.2 |
| | 50 | 92.3 |
| | 100 | 94.4 |
| BNT | 0 | 60.9 |
| | 5 | 63.3 |
| | 10 | 65.1 |
| | 25 | 65.4 |
| | 50 | 71.5 |
| | 100 | 75.1 |

(2) Image-Based Cell Analysis

The cultured LLC-PK1 cells in DMEM were dispensed in a 6-well plate at a density of $4 \times 10^5$ cells in 3 mL of the same DMEM medium per each well and then incubated under the same conditions for 24 hours to stabilize the cells. Next, after hypoxylonol F was added to 2.7 mL of the same DMEM medium at concentrations of 5 μM and 10 μM, and then incubated further for about 2 hours, 0.3 mL of the same DMEM medium in which 250 μM of cisplatin was previously dissolved was added thereto.

After incubation under the same conditions for about 24 hours, the cells were collected using trypsin, washed once with phosphate-buffered saline (PBS), resuspended in 100 μL of annexin-binding buffer (100 mM HEPES, 140 mM NaCl, 25 mM CaCl$_2$, pH 7.4) to reach a cell number of about $5 \times 10^5$ to about $5 \times 10^6$ cells/mL, and then mixed with 5 μL of Annexin V Alexa Fluor 488 and left in the dark at room temperature for about 20 minutes to fix and stain the cells. The resulting cell suspension was centrifuged to discard the supernatant and collect precipitated cell pellets. The precipitated cell pellets were resuspended in 100 μL of annexin-binding buffer to obtain a resuspension.

Next, 1 μL of propidium iodide (PI) was added to the resuspension, mixed thoroughly, and then left in the dark at room temperature for about 1 minute to about 5 minutes to fix and stain the cells. The stained cells were analyzed using a Tali Image-based cytometer and TaliPCApp (version 1.0) software.

Cells were divided into live cells (annexin V-negative/PI-negative), early apoptotic cells (annexin V-positive/PI-negative), and late apoptotic or necrotic cells (annexin V-positive/PI-positive), and total apoptotic cells were expressed as a ratio of annexin V-positive cells to PI-negative or PI-positive cells.

Figure 3A:
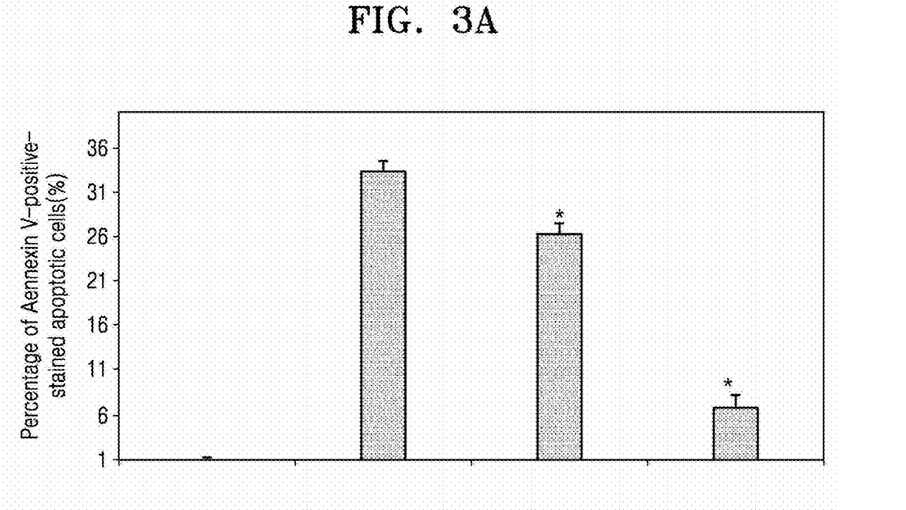
FIGS. 3A and 3B illustrate a graph and images, respectively, showing effects of hypoxylonol F and cisplatin on cell morphology and apoptosis in LLC-PK1 cells.
Figure 3B:
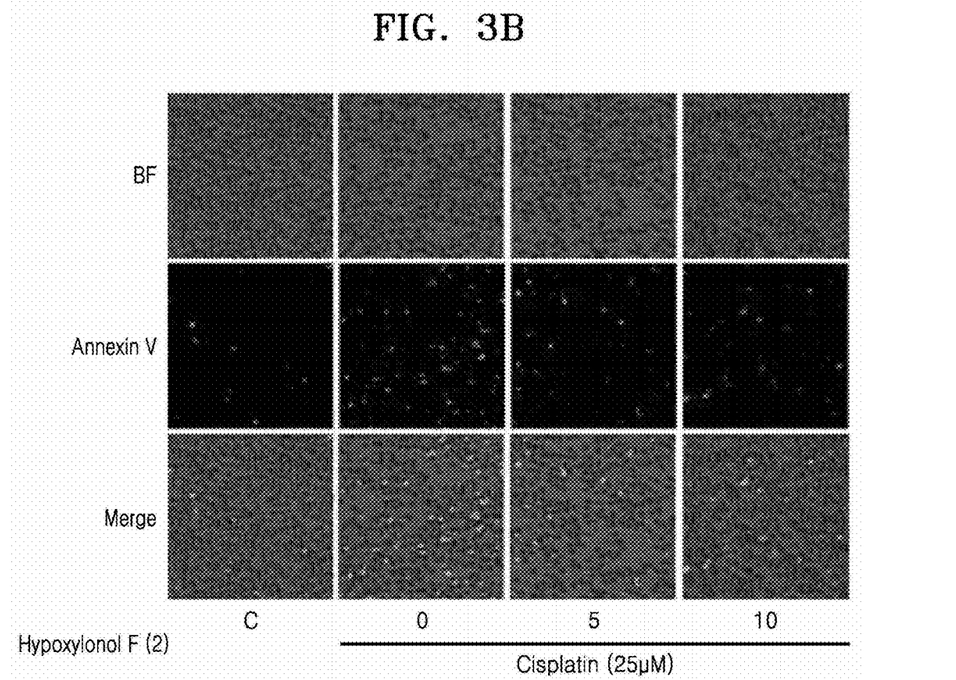

FIGS. 3A and 3B are a graph and images, respectively, showing effects of hypoxylonol F and cisplatin on cell shape and apoptosis in LLC-PK1 cells. As shown in FIG. 3B, in the control groups, most of the cells were found to have a normal nucleus having a round shape and intact cell membrane, with blue fluorescence. When treated with 25 μM of cisplatin, cells with condensed chromatin, a condensed nucleus and a damaged cell membrane, i.e., apoptotic cells, exhibited green fluorescence, due to being stained with PI. However, in the hypoxylonol F treatment groups at concentrations of 5 μM and 10 μM, the number of green-fluorescent cells, i.e., apoptotic cells, was reduced. Referring to FIG. 3A, in the samples, i.e., the hypoxylonol F treatment groups, apoptosis of the LLC-PK1 cells, caused by cisplatin, was significantly reduced. Table 2 shows apoptosis percentages in the hypoxylonol F treatment groups, based on FIG. 3A.

TABLE 2

| Compound | Concentration (μM) | Apoptosis (%) |
| --- | --- | --- |
| Hypoxylonol F | 0 | 33.3 |
| | 5 | 26.3 |
| | 10 | 6.6 |

(3) Protein Detection Test

The cultured LLC-PK1 cells in DMEM were dispensed in a 6-well plate at a density of $4 \times 10^5$ cells in 3 mL of the same DMEM medium per each well and then incubated under the same conditions for 24 hours to stabilize the cells. Next, after hypoxylonol F was added to 2.7 mL of the same medium at concentrations of 5 μM and 10 μM, and then incubated further for about 2 hours, 0.3 mL of the same medium in which 250 μM of cisplatin was previously dissolved was added thereto.

After incubation under the same conditions for about 24 hours, the cells were collected, and washed once with PBS, a radioimmunoprecipitation assay (RIPA) buffer (available from Cell Signaling, MA, USA) containing 1 mM phenylmethylsulfonyl fluoride was added thereto and left at about 4° C. for about 2 hours. The resulting reaction product was centrifuged at about 12,000 rpm for about 20 minutes to remove cell debris and collect only a supernatant. The supernatant was dried to obtain a soluble fraction of a cell lysate.

Figure 4:
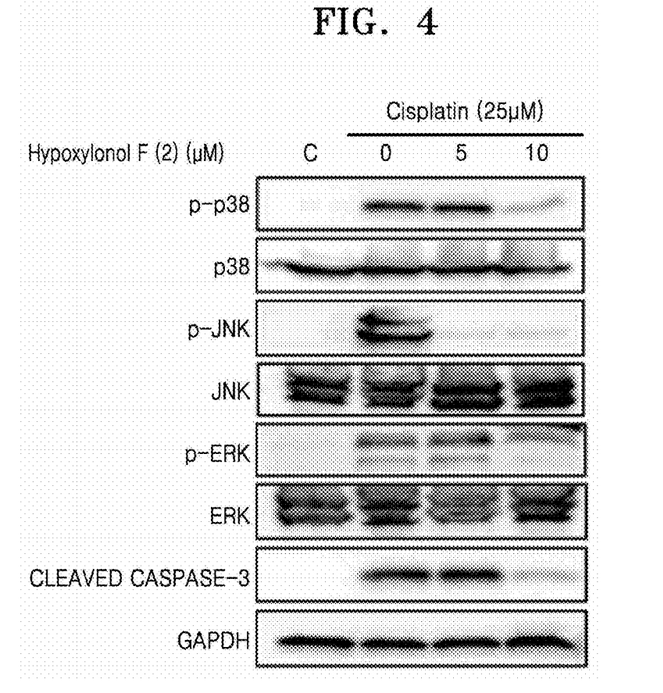
FIG. 4 illustrates Western blotting images showing effects of cisplatin and hypoxylonol F on protein expression in LLC-PK1 cells.
Figure 5:
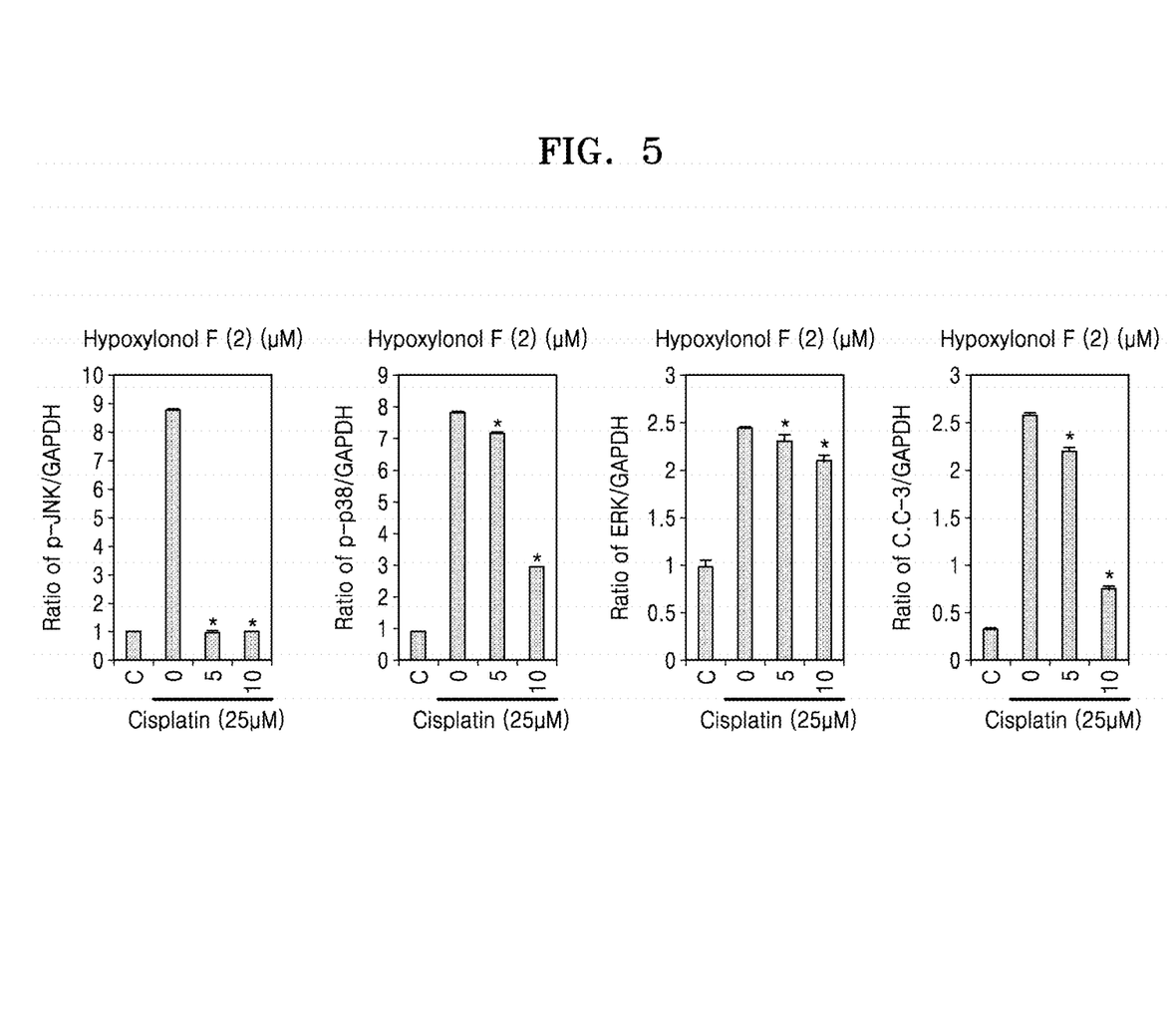
FIG. 5 illustrates graphs showing effects of cisplatin and hypoxylonol F on protein expression in LLC-PK1 cells.

Using the soluble fraction from cell lysate, proteins were quantified using a BCA protein assay kit (available from Thermo Scientific, Rockford, USA). 20 μg of the soluble fraction per well was subjected to sodium dodecyl sulfate-polyacrylamide gel electrophoresis (SDS-PAGE) to isolate denatured proteins. The isolated proteins were transferred to a polyvinylidene difluoride membrane (PVDF) membrane (available from Merck Millipore, Germany). To prevent non-specific binding of antibodies to this membrane, the membrane was incubated in a 5%-skim milk at room temperature for about 2 hours to block non-specific binding sites, and then washed three times, each for about 10 minutes with a Tris Buffered Saline with Tween 20 (TBST) buffer (containing 20 nM tris-HCl, 150 mM NaCl, and 0.05% Tween-20, pH 7.5). Next, to measure the levels of expression of P-P38, P38, P-JNK, JNK, P-ERK, ERK, intracellular cleaved caspase-3, and GAPDH, rabbit primary antibodies (available from Cell Signaling, Danvers, USA) binding to each protein were diluted in a ratio of 1:1,000, allowed to react with the membrane at room temperature for about 1 hour, and washed three times, each for about 10 minutes with the TBST buffer. Next, goat anti-rabbit IgG secondary antibodies (available from Calbiochem, La Jolla, Calif., USA) were diluted in a ratio of 1:2,000 and allowed to react with the membrane at room temperature for about 2 hours. Then, the proteins were identified using an ECL detection kit (available from GE healthcare). The results are shown in FIGS. 4 and 5. FIGS. 4 and 5 are Western blotting images and graphs, respectively, showing effects of cisplatin and hypoxylonol F on protein expression in the LLC-PK1 cells.

As described above, according to the one or more embodiments, a composition for preventing or reducing nephrotoxicity in a subject may efficiently prevent or reduce nephrotoxicity in the subject. A composition for preventing or reducing apoptosis of kidney cells in a subject may efficiently prevent or reduce apoptosis of kidney cells in the subject. A method of preventing or reducing kidney cell damage in a subject or ex vivo may efficiently prevent or reduce kidney cell damage in the subject or ex vivo.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of treating or reducing kidney cell damage in a subject or ex vivo, the method comprising contacting a composition with kidney cells,
wherein the composition comprises any stereoisomers of the group consisting of compounds represented by Formulae I, II, and III, or solvates, hydrates, mixtures, or pharmaceutically acceptable salts thereof:

[Formula I]

[Formula II]

[Formula III]

wherein, in Formulae I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or ($C_1$-$C_6$)-alkyl.

2. The method of claim 1, wherein the contacting comprises administering the composition to the subject.

3. The method of claim 1, wherein the kidney cells are proximal tubule cells.

4. The method of claim 2, further comprising administering a nephrotoxic compound to the subject.

5. The method of claim 4, wherein the nephrotoxic compound is selected from the group consisting of a platinum-based anticancer agent, gentamicin, an iodinated contrast agent, foscarnet, mannitol, amphotericin B, acetoaminophen, and chloroform.

6. The method of claim 4, wherein the administering of the composition is performed before, during, or after the administering of the nephrotoxic compound.

7. The method of claim 1, wherein the kidney cell damage is apoptosis of kidney cells.

8. A method for treating or reducing nephrotoxicity in a subject, the method comprising contacting a composition with kidney cells,
wherein the composition comprises any stereoisomers of the group consisting of compounds represented by Formulae I, II, and III, or solvates, hydrates, mixtures, or pharmaceutically acceptable salts thereof:

[Formula I]

[Formula II]

[Formula III]

wherein, in Formulae I, II, and III, $R_1$, $R_2$, $R_3$, $R_4$, $R_5$, $R_6$, $R_7$, $R_8$, $R_9$, $R_{10}$, $R_{11}$, and $R_{12}$ are each independently H or ($C_1$-$C_6$)-alkyl.

9. The method of claim 8, wherein $R_1$ and $R_3$ are each independently H or ($C_1$-$C_6$)-alkyl, and $R_2$, $R_3$, $R_4$, $R_6$, $R_7$, $R_8$, $R_9$, $R_{10}$, $R_{11}$, and $R_{12}$ are each H.

10. The method of claim 9, wherein $R_1$ and $R_3$ are each independently H, methyl, or ethyl.

11. The method of claim 8, wherein the compounds represented by Formulae I, II, and III are present in the composition in a weight ratio of 1.0:0.20 to 0.60:0.50 to 1.00.

12. The method of claim 8, wherein the composition further comprises a pharmaceutically acceptable carrier or diluent.

13. The method of claim 8, wherein the nephrotoxicity is caused by a nephrotoxic compound.

14. The method of claim 13, wherein the nephrotoxic compound is selected from the group consisting of a platinum-based anticancer agent, gentamicin, an iodinated contrast agent, foscarnet, mannitol, amphotericin B, acetoaminophen, and chloroform.

15. The method of claim 14, wherein the platinum-based anticancer agent is cis-diaminodichloroplatinum II (cisplatin), carboplatin, oxaliplatin, or nedaplatin.

16. The method of claim 8, wherein the composition reduces apoptosis of kidney cells.

17. The method of claim 8, wherein the nephrotoxicity is acute renal failure.

* * * * *